US012678775B2

(12) United States Patent
Karpov et al.

(10) Patent No.: US 12,678,775 B2
(45) Date of Patent: Jul. 14, 2026

(54) CATALYST EFFECTIVE IN THE OXIDATIVE CONVERSION OF ETHYLENE TO ETHYLENE OXIDE

(71) Applicant: BASF SE, Ludwigshafen am Rhein (DE)

(72) Inventors: Andrey Karpov, Ludwigshafen am Rhein (DE); Christian Walsdorff, Ludwigshafen am Rhein (DE); Michael Kraemer, Ludwigshafen am Rhein (DE); Armin Lange De Oliveira, Heidelberg (DE); Gerhard Krennrich, Ludwigshafen am Rhein (DE); Christian Bartosch, Ludwigshafen am Rhein (DE); Juergen Zuehlke, Ludwigshafen am Rhein (DE)

(73) Assignee: BASF SE, Ludwigshafen am Rhein (DE)

( * ) Notice: Subject to any disclaimer, the term of this patent is extended or adjusted under 35 U.S.C. 154(b) by 573 days.

(21) Appl. No.: 16/968,542

(22) PCT Filed: Feb. 6, 2019

(86) PCT No.: PCT/EP2019/052866

§ 371 (c)(1),
(2) Date: Aug. 7, 2020

(87) PCT Pub. No.: WO2019/154832

PCT Pub. Date: Aug. 15, 2019

(65) Prior Publication Data

US 2021/0046459 A1 Feb. 18, 2021

(30) Foreign Application Priority Data

Feb. 7, 2018 (EP) .................................... 18155531

(51) Int. Cl.
*B01J 21/04* (2006.01)
*B01J 23/656* (2006.01)
(Continued)

(52) U.S. Cl.
CPC ............ *B01J 23/688* (2013.01); *B01J 21/04* (2013.01); *B01J 23/6567* (2013.01);
(Continued)

(58) Field of Classification Search
CPC ....... B01J 21/04; B01J 23/6567; B01J 23/688
See application file for complete search history.

(56) References Cited

U.S. PATENT DOCUMENTS 4,728,634 A 3/1988 Boxhoorn et al.
4,732,918 A 3/1988 Lohmueller
(Continued)

FOREIGN PATENT DOCUMENTS

DE 2300512 A1 7/1973
DE 2454972 A1 6/1975
(Continued)

OTHER PUBLICATIONS

International Preliminary Report on Patentability received for PCT Patent Application No. PCT/EP2019/052866, mailed on Feb. 11, 2020, 5 pages.

(Continued)

*Primary Examiner* — Jun Li
(74) *Attorney, Agent, or Firm* — Faegre Drinker Biddle & Reath LLP

(57) ABSTRACT

The present invention provides a catalyst effective in the oxidative conversion of ethylene to ethylene oxide, comprising an alumina support and 20 to 45% by weight of the catalyst, of silver applied to the support, the catalyst meeting the following limitations (i) to (v): (i) an amount of cesium c(Cs) in mmol per Kg of catalyst of at least 2; (ii) an amount (Continued)

of rhenium c(Re) in mmol per Kg of catalyst of at least 3.0; (iii) an amount of tungsten c(W) in mmol per Kg of catalyst of at least 1.6; (iv) a silicon to alkaline earth metal molar ratio x of not higher than 1.80; (v) $c(Cs)-c(Re)-c(W) \leq 4 \cdot x - 0.5$.

10 Claims, 1 Drawing Sheet

(51) Int. Cl.
*B01J 23/68* (2006.01)
*B01J 35/10* (2006.01)
*B01J 35/61* (2024.01)
*B01J 37/02* (2006.01)
*B01J 37/08* (2006.01)
*C07D 301/10* (2006.01)

(52) U.S. Cl.
CPC ......... *B01J 35/612* (2024.01); *B01J 37/0201* (2013.01); *B01J 37/088* (2013.01); *C07D 301/10* (2013.01); *B01J 2235/00* (2024.01)

(56) References Cited

U.S. PATENT DOCUMENTS

| | | | | |
|---|---|---|---|---|
| 4,761,394 | A * | 8/1988 | Lauritzen | B01J 23/688 502/348 |
| 4,766,105 | A | 8/1988 | Lauritzen | |
| 4,908,343 | A | 3/1990 | Bhasin | |
| 5,100,859 | A | 3/1992 | Gerdes et al. | |
| 5,187,140 | A | 2/1993 | Thorsteinson et al. | |
| 5,504,052 | A | 4/1996 | Rizkalla et al. | |
| 5,646,087 | A | 7/1997 | Rizkalla et al. | |
| 5,801,259 | A | 9/1998 | Kowaleski | |
| 7,553,795 | B2 | 6/2009 | Bortinger et al. | |
| 7,714,152 | B2 | 5/2010 | Pak | |
| 7,932,408 | B2 | 4/2011 | Christian | |
| 7,977,274 | B2 | 7/2011 | Gueckel | |
| 8,378,129 | B2 | 2/2013 | Bhise et al. | |
| 8,546,297 | B2 | 10/2013 | Rokicki et al. | |
| 2008/0154051 | A1* | 6/2008 | Bolk | C07D 301/06 549/534 |
| 2012/0264954 | A1* | 10/2012 | Rosendahl | B01J 37/0203 502/317 |
| 2013/0296587 | A1 | 11/2013 | Rosendahl et al. | |
| 2014/0179516 | A1 | 6/2014 | Nakashiro et al. | |
| 2014/0187417 | A1 | 7/2014 | Pak | |
| 2016/0297781 | A1* | 10/2016 | Zakzeski | B01J 27/047 |
| 2017/0056860 | A1* | 3/2017 | Nagy | B01J 21/16 |
| 2018/0161761 | A1* | 6/2018 | Yeates | B01J 35/612 |

FOREIGN PATENT DOCUMENTS

| | | | | |
|---|---|---|---|---|
| DE | 2521906 | A1 | 12/1975 | |
| DE | 3414717 | A1 | 10/1985 | |
| EP | 0014457 | A2 | 8/1980 | |
| EP | 0082609 | A1 | 6/1983 | |
| EP | 0085237 | A1 | 8/1983 | |
| EP | 0172565 | A2 | 2/1986 | |
| EP | 0266015 | A1 | 5/1988 | |
| EP | 0266852 | A1 * | 5/1988 | C07D 301/10 |
| EP | 0339748 | A2 | 11/1989 | |
| EP | 0357293 | A1 | 3/1990 | |
| EP | 0480538 | A1 | 4/1992 | |
| EP | 0902726 | A1 | 3/1999 | |
| EP | 1511563 | A2 | 3/2005 | |
| EP | 1893331 | A1 | 3/2008 | |
| EP | 3254756 | A1 | 12/2017 | |
| GB | 1512625 | A | 6/1978 | |
| WO | 97/46316 | A1 | 12/1997 | |
| WO | 03/72246 | A2 | 9/2003 | |
| WO | 2004/089539 | A1 | 10/2004 | |
| WO | 2004/101144 | A1 | 11/2004 | |
| WO | 2006/036667 | A1 | 4/2006 | |
| WO | 2006/133183 | A2 | 12/2006 | |
| WO | 2007/000664 | A1 | 1/2007 | |
| WO | 2007/122090 | A2 | 11/2007 | |
| WO | 2007/123932 | A2 | 11/2007 | |
| WO | 2010/123729 | A2 | 10/2010 | |
| WO | 2010/123856 | A1 | 10/2010 | |
| WO | 2011/153390 | A2 | 12/2011 | |
| WO | 2012/091898 | A2 | 7/2012 | |
| WO | 2012/140614 | A1 | 10/2012 | |
| WO | 2012/143557 | A1 | 10/2012 | |
| WO | 2012/143559 | A1 | 10/2012 | |
| WO | 2013/061294 | A1 | 5/2013 | |
| WO | WO-2015087194 | A1 * | 6/2015 | C07D 301/10 |

OTHER PUBLICATIONS

International Search Report and Written Opinion received for PCT Patent Application No. PCT/EP2019/052866, mailed on Apr. 25, 2019, 9 pages.

* cited by examiner

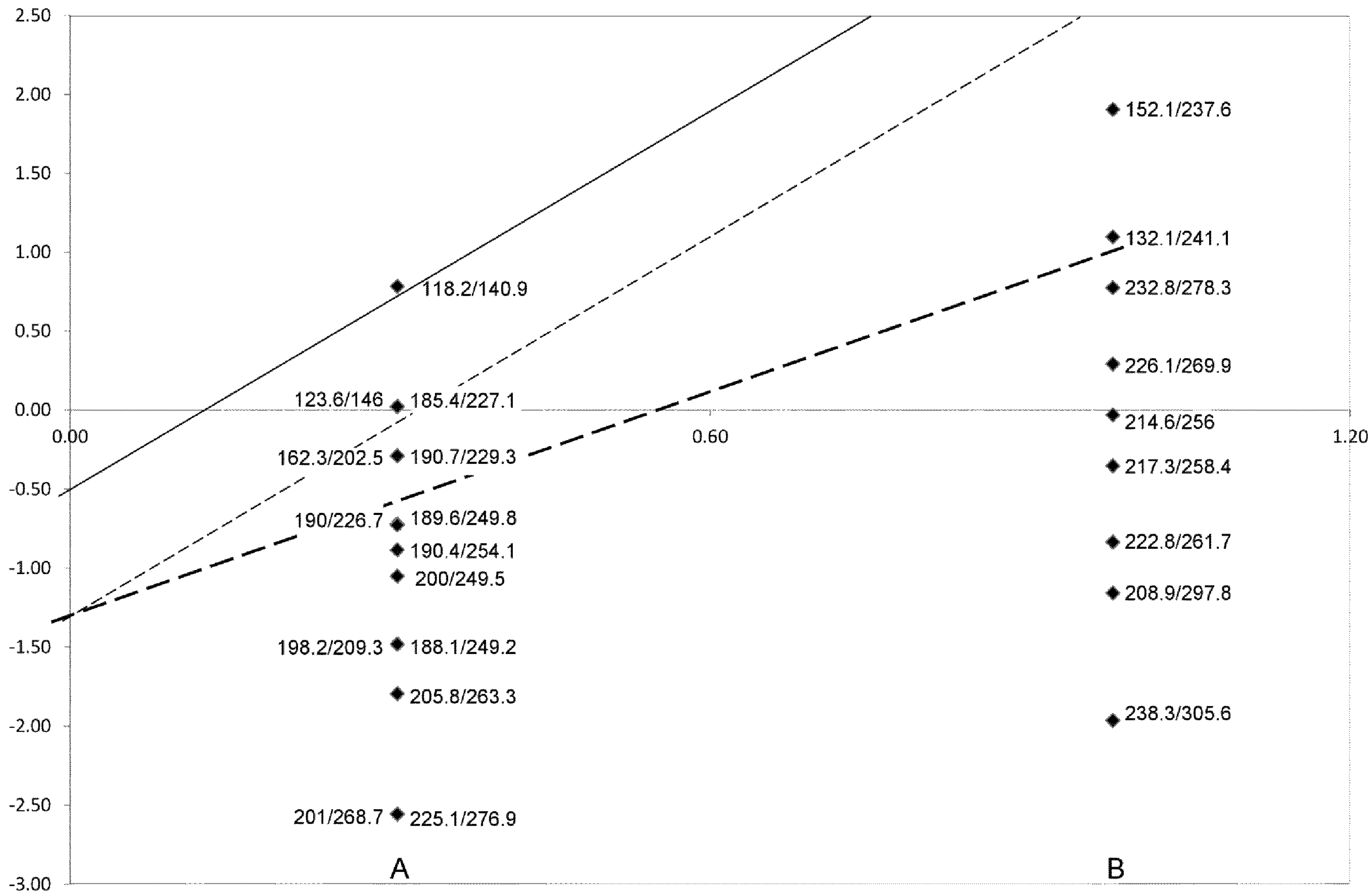
2.50
2.00
1.50
1.00
0.50
0.00
-0.50
-1.00
-1.50
-2.00
-2.50
-3.00
0.00
0.60
1.20
118.2/140.9
123.6/146
185.4/227.1
162.3/202.5
190.7/229.3
190/226.7
189.6/249.8
190.4/254.1
200/249.5
198.2/209.3
188.1/249.2
205.8/263.3
201/268.7
225.1/276.9
A
152.1/237.6
132.1/241.1
232.8/278.3
226.1/269.9
214.6/256
217.3/258.4
222.8/261.7
208.9/297.8
238.3/305.6
B

CATALYST EFFECTIVE IN THE OXIDATIVE CONVERSION OF ETHYLENE TO ETHYLENE OXIDE

CROSS-REFERENCE TO RELATED APPLICATIONS

This application is a national stage application (under 35 U.S.C. § 371) of PCT/EP2019/052866, filed Feb. 6, 2019, which claims benefit of European Application No. 18155531.9, filed Feb. 7, 2018, both of which are incorporated herein by reference in their entirety.

The present invention relates to a catalyst effective in the oxidative conversion of ethylene to ethylene oxide, a method for preparing the catalyst, and a process for preparing ethylene oxide by gas-phase oxidation of ethylene by means of oxygen in the presence of the catalyst.

Ethylene oxide is an important basic chemical and is prepared on an industrial scale by direct oxidation of ethylene with oxygen in the presence of silver-containing catalysts. These catalysts comprise metallic silver, which has been deposited on a support material by means of a suitable process. Apart from silver as active component, these catalysts often comprise minor amounts of promoting species for improving the catalytic properties of the catalyst. See, for example, WO 2007/122090 or WO 2010/123856. Examples of promoting species are alkali metal compounds and/or alkaline earth metal compounds. Some documents teach the use of transition metals such as cobalt (EP 0 480 538), tungsten or molybdenum. A particularly preferred promoter for influencing the activity and selectivity of catalysts is rhenium. In industry, preference is given to using catalysts comprising rhenium and/or other transition metal promoters in combination with alkali metal compounds and/or alkaline earth metal compounds because of their high selectivity.

US 2013/0296587 A1 describes a tungsten-free catalyst for the epoxidation of alkenes, which comprises silver, molybdenum and tin applied to a support and which displays advantageous activity and selectivity.

U.S. Pat. No. 4,728,634 describes ethylene oxide catalysts comprising silver, alkali metal promoters supported on a carrier, which carrier is prepared by a process which comprises mixing an aluminum compound with an alkali metal salt and with a silicon compound and calcining resultant mixture at a temperature greater than about 1100° C.

U.S. Pat. No. 4,908,343 describes a catalyst for the manufacture of ethylene oxide which contains impregnated silver on a support and a mixture of cesium salt and one or more of alkali metal and alkaline earth metal salt in which the anions thereof are halide or selected from specific oxyanions. Ten different carriers are described (carriers A to I). Data about the compositions of these carriers is incomplete. Alpha-alumina impurities in bulk are provided only for carriers A and C. For carrier C, these impurities include 0.01 wt % of $SiO_2$ and 0.03 wt % Oxides of Ca and Mg. Catalysts prepared from carrier C do not contain any tungsten and only from 13.4 to 13.89% of added silver.

US 2012/0264954 A1 describes a shaped catalyst body for preparing ethylene oxide, which comprises at least silver and rhenium applied to an alumina support, wherein the alumina support has the geometry of a hollow cylinder and wherein the rhenium content is adjusted specifically to the wall thickness of the hollow cylinder. Particularly preferably, the shaped catalyst body comprises silver in an amount of from 10 to 20% by weight, calculated as element and based on the total weight of shaped catalyst body. Ca, Mg, and Si contents of the supports used are indicated. All exemplified catalysts contain tungsten in an amount of 200 ppm by weight.

U.S. Pat. No. 5,801,259 describes an ethylene oxide catalyst which contains silver and one or more alkali metal promoters supported on a carrier prepared by a process comprising the use of ceramic particle components with particle sizes chosen to ensure that a desired degree of porosity is obtained without the use of organic burnout materials. None of the exemplified catalysts contains tungsten. The exemplified catalysts contain 13.2 to 14.5 wt % of silver.

U.S. Pat. No. 4,766,105 describes an ethylene oxide catalyst comprising silver, a promoting amount of alkali metal, a promoting amount of rhenium and a promoting amount of rhenium co-promotor selected from sulfur, molybdenum, tungsten, chromium and mixtures thereof supported on a porous refractory support. Alkaline earth metal contents are not defined for the exemplified alpha-alumina-containing carriers A, B, C, D, E, and F described in table 1. Examples in which the co-promotor is tungsten (experiments no. 7-11, 7-17, 7-24, 7-26; table 7) were carried out utilizing carrier B described in table 1.

WO 2007/123932 A2 describes a supported silver catalyst prepared on an alumina-containing carrier, the carrier comprising greater than about 80 weight percent alpha-alumina and less than about 30 parts per million acid-leachable alkali metals by weight, wherein the acid-leachable alkali metals are selected from lithium, sodium, potassium, and mixtures thereof. Alkaline earth metal oxides are mentioned as a common impurity of the carrier without giving any quantity.

WO 2013/061294 A1 describes a process for producing a supported silver catalyst. Exemplified calcined catalysts contained 15.5% Ag, 190 ppm Li, 14 ppm S, 200 ppm W, 350 ppm Cs, and 310 ppm Re.

US 2014/0179516 A1 describes a catalyst for producing ethylene oxide from ethylene which is composed of at least silver (Ag), cesium (Cs), rhenium (Re) and a carrier, and can be improved, in particular, in selectivity. The catalyst comprises silver (Ag), cesium (Cs), rhenium (Re) and a carrier, said catalyst being produced by optionally pretreating the carrier to support an alkali metal thereon and then supporting Ag, Cs and Re on the carrier. The carrier has a specific surface area of 0.6 to 3.0 $m^2/g$ and a weight ratio of a silicon (Si) content to a sodium (Na) content of 2 to 50 in terms of $SiO_2/Na_2O$; the content of Re in the catalyst is 170 to 600 ppm per 1 $m^2/g$ of the specific surface area of the carrier; and the molar ratio of Cs to Re in the catalyst is 0.3 to 19.

WO 2004/089539 describes a silver-catalyst composition comprising a support and deposited on the support: silver metal, a metal or component comprising rhenium, tungsten, molybdenum or a nitrate- or nitrite-forming compound, and a group IA metal or component comprising a group IA metal having an atomic number of at least 37, and in addition potassium. All exemplified catalysts contained 13.2% by weight of silver. Substitution of a well-defined portion of a higher group IA metal comprised by a silver-based epoxidation catalyst for potassium is suggested and it is explained that this substitution would improve initial activity of the catalyst, performance of the catalyst in the course of its lifetime and the lifetime of the catalyst itself. One of the supports of the exemplified catalysts was prepared as described in U.S. Pat. No. 5,100,859. The support used in example 10 was prepared by mixing alpha alumina, boehmite, ammonium stabilized silica sol, and sodium acetate.

U.S. Pat. No. 5,100,859 describes an alpha-alumina carrier for silver-containing catalysts used in the preparation of ethylene oxide. The carrier comprises at least about 85% by weight of alpha alumina, from about 0.01 to about 6 percent by weight (measured as the oxide) of an alkaline earth metal oxide which is defined to include mixed oxides such as a preferred silicate; from about 0.01 to about 5% by weight, (measured as silica) of a silicon oxide, including mixed oxides such as the silicates. The alpha alumina powder is preferably combined with calcium silicate itself. All exemplified catalysts contained 10.0 to 14.5 wt % of silver. The catalysts did not contain any tungsten.

U.S. Pat. No. 5,187,140 describes catalysts for the epoxidation of alkene, especially ethylene, to the corresponding alkylene oxide, e.g., ethylene oxide, which catalysts contain a high silver content on carriers having a high surface area and a high pore volume. Silicon, calcium and magnesium content not determined for the exemplified carriers, except for carrier AC which was used in examples 79 to 84. None of the catalysts of examples 79 to 84 contained tungsten. Carrier AC displayed $SiO_2$-content of <0.05 wt %, CaO-content of 0.1 wt % and MgO-content of <0.02 wt % corresponding to Si-content of <234 ppm, Ca-content of 715 ppm and Mg-content of <120 ppm. In addition, carrier AC displayed $Na_2O$-content of 0.2 wt % corresponding to Na-content of 1484 ppm.

The problem underlying the present invention is the provision of a catalyst for preparing alkylene oxides which allows for a more efficient production of alkylene oxides and, in particular, at high EO-space-time-yields even at low temperature, i.e. with a prospect of prolonged catalyst lifetime.

The above problem is solved by a catalyst effective in the oxidative conversion of ethylene to ethylene oxide, which comprises an alumina support and 20 to 45% by weight of the catalyst, of silver applied to the support, the catalyst meeting the following limitations (i) to (v):

(i) an amount of cesium c(Cs) in mmol per Kg of catalyst of at least 2;

(ii) an amount of rhenium c(Re) in mmol per Kg of catalyst of at least 3.0, in particular at least 3.75;

(iii) an amount of tungsten c(W) in mmol per Kg of catalyst of at least 1.6;

(iv) a silicon to alkaline earth metal molar ratio x of not higher than 1.80;

(v) $c(Cs)-c(Re)-c(W)\leq 4\cdot x-0.5$ (Inequation I).

In a preferred embodiment, $$c(\mathrm{Cs})-c(\mathrm{Re})-c(\mathrm{W})\leq 4\cdot x-1.3.$$

In a still more preferred embodiment, $$c(\mathrm{Cs})-c(\mathrm{Re})-c(\mathrm{W})\leq 2.35\cdot x-1.3.$$

According to the invention, the catalyst comprises 20 to 45% by weight of the catalyst, of silver. A preferred catalyst comprises 22 to 35% by weight of the catalyst, of silver. Most preferably, the catalyst comprises 23 to 30% by weight by weight of the catalyst, of silver, e.g., 24 to 29% by weight of silver.

The catalyst of the invention comprises an amount of cesium c(Cs) in mmol per Kg of catalyst of at least 2. In a preferred catalyst, c(Cs) is at least 3. In a particularly preferred catalyst, c(Cs) is at least 4. Typically, c(Cs) is not higher than 15, preferably not higher than 13. In a preferred embodiment, c(Cs) is 4.5 to 11.3, in a more preferred embodiment, c(Cs) is 5 to 10, in a particularly preferred embodiment, c(Cs) is 5.5 to 8.5.

The catalyst of the invention comprises an amount of rhenium c(Re) in mmol per Kg of catalyst of at least 3.0. In a preferred catalyst, c(Re) is at least 3.3, in particular at least 3.75. Typically, c(Re) is not higher than 9.0, preferably not higher than 8.5, in particular not higher than 8.0. In a preferred embodiment, c(Re) is 3.75 to 7.5, in a particularly preferred embodiment, c(Re) is 4.0 to 7.0.

The catalyst of the invention comprises an amount of tungsten c(W) in mmol per Kg of catalyst of at least 1.6. In a preferred catalyst, c(W) is at least 1.9. In a particularly preferred catalyst, c(W) is at least 2.2. Typically, c(W) is not higher than 5.5, preferably not higher than 4.5, in particular not higher than 3.9. Usually, c(W) is 1.6 to 5.5, preferably 1.9 to 4.5, most preferably 2.2 to 3.9. In a particularly preferred embodiment, c(W) is 2.75 to 3.25.

For catalysts of the invention, the Cs:Re:W molar ratio is preferably 12 to 19:9 to 12.5:4 to 6.

The silicon to alkaline earth metal molar ratio of the catalyst may vary in broad ranges. Preferably, x is 0.1 to 1.6, more preferably 0.1 to 1.46, most preferably 0.2 to 1.20. For a particular catalyst of the invention, x is in a range from 0.1 to 1.2, in particular from 0.8 to 1.1. The alkaline earth metals are mainly calcium and/or magnesium, and other alkaline earth metals, such as beryllium, strontium and barium, can practically be neglected. Thus, x is the silicon to (calcium+magnesium) molar ratio.

It has been found that high EO-space-time-yields are obtained when the relative amounts of cesium, rhenium, tungsten, silicon and alkaline earth metals are adjusted to meet the inequation (I) above. This is illustrated in FIG. 1 where each black square below the straight solid line represents a catalyst of the invention.

The catalyst of the invention can comprise sodium and/or potassium. The amount of sodium and/or potassium is not particularly limited and can range, for example, from a total amount of 1 mmol per Kg of catalyst to 30 mmol per Kg of catalyst. The catalyst of the invention can comprise an amount of potassium c(K) in mmol per Kg of catalyst of 2.6 to 10.3, preferably 3.5 to 6.4. It will be appreciated that c(K) includes the potassium contributed by the alumina carrier and the potassium contributed by the impregnation solution described later.

Low potassium contents are desired in particular when x is small, e.g., when the silicon to alkaline earth metal molar ratio is less than 0.6. In such catalysts, c(K) typically is not higher than 4.60, preferably not higher than 4.25, in particular not higher than 3.95.

The catalyst of the invention can comprise an amount of sodium c(Na) in mmol per Kg of catalyst of 0.2 to 10, preferably 0.3 to 5.0, e.g. 0.43 to 4.3. It will be appreciated that c(Na) includes the sodium contributed by the alumina carrier and the sodium contributed by the impregnation solution described later.

The amount of sodium comprised by the inventive catalyst can also be expressed as amount of sodium $c(Na)_{Ag}$ in mmol per Kg of silver comprised by the catalyst. $c(Na)_{Ag}$ is, for example, in a range from 1 to 50, preferably from 2 to 25, more preferably from 3 to 20, most preferably from 5 to 15.

The catalyst of the invention may comprise lithium. The catalyst comprises, for example, an amount of lithium c(Li) in mmol per Kg of catalyst of 20 to 100, preferably of 43 to 86, most preferably of 55 to 80.

Preferably, the amount of calcium c(Ca) in mmol per Kg of catalyst is from 1 to 20, preferably 2 to 10. Preferably, the amount of magnesium c(Mg) in mmol per Kg of catalyst is from of 1 to 20, preferably 2 to 10.

The catalyst of the invention may further comprise sulfur. The catalyst comprises, for example, an amount of sulfur c(S) in mmol per Kg of catalyst of from 0.3 to 3, preferably of 0.4 to 2.5, in particular of 0.5 to 2.0, most preferably of 0.6 to 1.5.

The amount of promotors relative to silver is not particularly limited. Preferably, the sum of the masses of rhenium and cesium comprised by the catalyst is above 0.43% relative to the mass of the silver comprised by the catalyst, for example, from 0.53% to 0.91%, in particular from 0.60% to 0.91% of the mass of the silver comprised by the catalyst.

In preferred catalysts of the invention, the molar amount of cesium comprised by the catalyst exceeds the molar amount of rhenium comprised by the catalyst, and the molar excess of cesium over rhenium is at most 14.0 μmol of cesium per gram of silver comprised by the catalyst, preferably at most 10.5 μmol of cesium per gram of silver comprised by the catalyst.

The present invention further relates to a method for preparing a catalyst according to any of the preceding claims, comprising:

(a) impregnating an alumina support having a silicon to alkaline earth metal molar ratio x of not higher than 1.80 with a silver impregnation solution, the silver impregnation solution containing sources of cesium, rhenium and tungsten;

(b) calcining the impregnated alumina support.

The alumina support used in step (a) preferably comprises 100 to 1000 ppm of calcium per total support weight, and/or 50 to 500 ppm of magnesium per total support weight.

Alumina supports having a desired silicon to alkaline earth metal molar ratio x and calcium or magnesium content as specified above are commercially available from, e.g., Saint-Gobain NorPro, CeramTec, Noritake, and Exacer.

Preferably, the alumina support used in step (a) is in the form of shaped pellets, for example, cylinders, rings, trilobes, tetralobes and the like. Examples of suitable geometries are provided in WO2004/101144, WO2006/036667, or WO2012/091898. Particular preference is given to hollow cylinders having the following geometries (external diameter×length×internal diameter, in each case reported in mm): 5×5×1.8, 6×6×2, 7×7×2.5, 7×7.5×2.5, 7.7×7×2.5, 7.5×7.5×2.5, 7×7×3, 7×7.5×3.0, 7.5×7×3.0, 7.5×7.5×3.0, 8×8×2.8, 8×8.5×2.8, 8.5×8×2.8, 8.5×8.5×2.8, 8×8×3, 8×8.5×3, 8.5×8×3, 8.5×8.5×3, 8×8×3.3, 8×8.5×3.3, 8.5×8×3.3, 8.5×8.5×3.3, 8.5×9×3, 9×8.5×3, 9×9×3, 9×9.5×3, 9.5×9×3, 9×9.5×3.5, 9.5×9×3.5. Each length indicated is subject to tolerances in the region of ±0.5 mm. According to the invention, it is also possible for the catalyst to be used in the form of crushed catalyst material obtained from one or more of the shaped bodies mentioned.

The preparation of the catalysts as such is known in the art and the known methods are applicable to the preparation of the catalyst of this invention. Methods of preparing the catalyst include impregnating the support with a silver impregnation solution, and performing a reduction to form metallic silver particles. The reduction of cationic silver to metallic silver may be accomplished during a step in which the catalyst composition is dried, so that the reduction as such does not require a separate process step. This may be the case if the impregnation solution comprises a reducing agent, for example, an oxalate.

Rhenium and tungsten may suitably be provided as an oxyanion, for example, as a perrhenate or tungstate in salt or acid form. Cesium may suitably be provided as cesium hydroxide.

The alumina support used in step (a) comprises silicon and contributes more than 50%, preferably more than 60%, most preferably more than 70% and in particular more than 80% of the silicon comprised by the catalyst.

The alumina support used in step (a) comprises sodium and contributes more than 50%, preferably more than 60%, most preferably more than 70% and in particular more than 80% of the sodium comprised by the catalyst.

The alumina support used in step (a) comprises calcium and contributes more than 50%, preferably more than 60%, most preferably more than 70% and in particular more than 80% of the calcium comprised by the catalyst.

The alumina support used in step (a) comprises magnesium and contributes more than 50%, preferably more than 60%, most preferably more than 70% and in particular more than 80% of the magnesium comprised by the catalyst.

On the other hand, the impregnation solution contributes more than 50%, preferably more than 60%, most preferably more than 70% and in particular more than 80% of the amounts of cesium, lithium, rhenium and tungsten comprised by the final catalyst.

Neither the BET surface area nor the water absorption of the support is particularly limited. It is nevertheless assumed that certain ranges of BET surface area of the alumina support and of the water absorption of the alumina support are preferred in order to provide an overall improved catalyst which provides very high EO-space-time-yields but still has very high crushing strength.

The BET surface area of the alumina support used in step (a) is preferably from 1.5 to 2.5 $m^2/g$, more preferably from 1.7 to 2.3 $m^2/g$, most preferably at least 2.0 $m^2/g$, e.g., 2.0 to 2.2 $m^2/g$. If not noted otherwise stated, the BET surface is determined according to DIN ISO 9277 in the context of the present invention.

The water absorption of the alumina support used in step (a) can, for example, be in the range from 0.35 ml/g to 0.70 ml/g (ml of water/gram of support), preferably in the range from 0.38 ml/g to 0.65 ml/g, most preferably in the range from 0.41 to 0.60 ml/g. Water absorption refers to vacuum cold water uptake. Vacuum cold water uptake is determined by placing about 100 g of support (=initial support weight) in a rotating flask, covering the support with DI water, rotating the rotary evaporator for 5 minutes at about 30 rotations per minute, applying vacuum of 80 mbar for 3 minutes, transferring water and support into a glass funnel, keeping the support in the funnel for about 5 minutes with occasional shaking in order to ensure that adhering water runs down the funnel and then weighing the supports (=final support weight). The water absorption is calculated by subtracting the initial support weight from the final support weight and then dividing this difference by the initial support weight.

The ratio of water absorption of the alumina support (ml of water/gram of support) to BET surface area of the alumina support used in step (a) ($m^2$ of support/gram of support) is in the range from 0.18 to 0.33 $ml/m^2$, preferably in the range from 0.20 to 0.30 $ml/m^2$.

It is possible to establish the desired composition of the catalyst with relative amounts of all metals as defined in formula (I) in only one impregnation.

Alternatively, the alumina support is subjected to at least two subsequent impregnations. In subsequent impregnations, an impregnation step (a) is followed by a calcination step (b) and the calcined impregnated support obtained in step (b) is then passed to step (a) of a subsequent impregnation. Impregnation steps (a) and calcination steps (b) are repeated until the desired composition of the catalyst with relative amounts of all metals as defined in formula (I) is established. The composition of the impregnation medium used in a later impregnation step can be the same or different from the impregnation medium used in the initial impregnation step.

The impregnated support obtained after (the last) impregnation step (a), is calcined in order to obtain the catalyst of the invention. Any calcination processes known in the art can be used. Suitable examples of calcination processes are described in U.S. Pat. Nos. 5,504,052, 5,646,087, 7,553,795, 8,378,129, 8,546,297, US2014/0187417, EP 1893331 or WO2012/140614. Calcination preferably involves heating of the impregnated support to a temperature in the range from 250° C. to 330° C., preferably from 270° C. to 310° C. and maintaining this temperature for at least 1 minute, preferably for at least 2 minutes to at most 30 minutes. Calcination is preferably carried out in an inert atmosphere, e.g., in an $N_2$ atmosphere.

The invention also relates to a process for preparing ethylene oxide by gas-phase oxidation of ethylene by means of oxygen in the presence of the inventive catalyst.

According to the invention, the epoxidation can be carried out by all processes known to those skilled in the art. It is possible to use all reactors which can be used in the ethylene oxide production processes of the prior art; for example externally cooled shell-and-tube reactors (cf. Ullmann's Encyclopedia of Industrial Chemistry, 5th edition, vol. A-10, pp. 117-135, 123-125, VCH-Verlagsgesellschaft, Weinheim 1987) or reactors having a loose catalyst bed and cooling tubes, for example the reactors described in DE-A 3414717, EP 0082609 and EP-A 0339748. The epoxidation is preferably carried out in at least one tube reactor, preferably in a shell-and-tube reactor. To prepare ethylene oxide from ethylene and oxygen, it is possible according to the invention to carry out the reaction under conventional reaction conditions as described, for example, in DE-A 2521906, EP-A 0 014 457, DE-A 2300512, EP-A 0 172 565, DE-A 2454972, EP-A 0 357 293, EP-A 0 266 015, EP-A 0 085 237, EP-A 0 082 609 and EP-A 0 339 748. Inert gases such as nitrogen or gases which are inert under the reaction conditions, e.g. steam, methane, and also optionally reaction moderators, for example halogenated hydrocarbons such as ethyl chloride, vinyl chloride or 1,2-dichloroethane can additionally be mixed into the reaction gas comprising ethylene and molecular oxygen. The oxygen content of the reaction gas is advantageously in a range in which no explosive gas mixtures are present. A suitable composition of the reaction gas for preparing ethylene oxide can, for example, comprise an amount of ethylene in the range from 10 to 80% by volume, preferably from 20 to 60% by volume, more preferably from 25 to 50% by volume and particularly preferably in the range from 25 to 40% by volume, based on the total volume of the reaction gas. The oxygen content of the reaction gas is advantageously in the range of not more than 10% by volume, preferably not more than 9% by volume, more preferably not more than 8% by volume and very particularly preferably not more than 7.5% by volume, based on the total volume of the reaction gas. The reaction gas preferably comprises a chlorine-comprising reaction moderator such as ethyl chloride, vinyl chloride or dichloroethane in an amount of from 0 to 15 ppm by weight, preferably in an amount of from 0.1 to 8 ppm by weight. The remainder of the reaction gas generally comprises hydrocarbons such as methane and also inert gases such as nitrogen. In addition, other materials such as steam, carbon dioxide or noble gases can also be comprised in the reaction gas. The above-described constituents of the reaction mixture may optionally each have small amounts of impurities. Ethylene can, for example, be used in any degree of purity suitable for the gas-phase oxidation according to the invention. Suitable degrees of purity include, but are not limited to, "polymer-grade" ethylene which typically has a purity of at least 99% and "chemical-grade" ethylene which typically has a purity of less than 95%. The impurities typically comprise, in particular, ethane, propane and/or propene.

The reaction or oxidation of ethylene to ethylene oxide is usually carried out at elevated temperature. Preference is given to temperatures in the range from 150 to 350° C., more preferably 25 in the range from 180 to 300° C., more preferably temperatures in the range from 190° C. to 280° C. and particularly preferably temperatures in the range from 200° C. to 280° C. The present invention therefore also provides a process as described above in which the oxidation is carried out at a temperature in the range 180-300° C., preferably in the range from 200 to 280° C.

The reaction according to the invention (oxidation) is preferably carried out at pressures in the range from 5 bar to 30 bar. The oxidation is more preferably carried out at a pressure in the range from 5 bar to 25 bar, preferably at a pressure in the range from 10 bar to 20 bar and in particular in the range from 14 bar to 20 bar. The present invention therefore also provides a process as described above in which the oxidation is carried out at a pressure in the range from 14 bar to 20 bar.

The oxidation is preferably carried out in a continuous process. If the reaction is carried out continuously, the GHSV (gas hourly space velocity) is, depending on the type of reactor chosen, for example on the size/cross-sectional area of the reactor, the shape and size of the catalyst, preferably in the range from 800 to 10 000/h, preferably in the range from 2000 to 6000/h, more preferably in the range from 2500 to 5000/h, where the values indicated are based on the volume of the catalyst.

According to a further embodiment, the present invention is also directed to a process for preparing ethylene oxide by gas-phase oxidation of ethylene by means of oxygen as disclosed above, wherein the EO-space-time-yield measured is greater than 180 $kg_{EO}/(m^3_{cat}h)$, preferably to an EO-space-time-yield of greater than 200 $kd_{EO}/(m^3_{cat}h)$.

The preparation of ethylene oxide from ethylene and oxygen can advantageously be carried out in a recycle process. Here, the reaction mixture is circulated through the reactor with the newly formed ethylene oxide and also the by-products formed in the reaction being removed from the product gas stream after each pass and the product gas stream being, after having been supplemented with the required amounts of ethylene, oxygen and reaction moderators, reintroduced into the reactor. The separation of the ethylene oxide from the product gas stream and its work-up can be carried out by customary methods of the prior art (cf. Ullmann's Encyclopedia of Industrial Chemistry, 5th edition, vol. A-10, pp. 117-135, 123-125, VCH-Verlagsgesellschaft, Weinheim 1987).

The invention will be described in more detail by the accompanying drawings and the subsequent examples.

FIG. 1 shows EO-space-time-yields [$kg_{EO}/(m^3_{cat}h)$] for all catalysts tested in a two dimensional plot of the silicon to alkaline earth metal molar ratio x [horizontal axis] vs. the difference c(Cs)−c(Re)−c(W) [vertical axis].

According to FIG. 1, the numbers at each of the black squares are EO-space-time-yields measured at 230° C. and 235° C., respectively. It is apparent that EO-space-time-yield is higher for the catalysts which are within the limitation of inequation (I) than for the catalyst which is not within this limitation. The catalyst of example 3.3.8 is not within the limitation of inequation (I). The EO-space-timeyield of this catalyst was less satisfactory, i.e. 118.2 $kg_{EO}/(m^3_{cat}h)$ at 230° C. and 140.9 $kg_{EO}/(m^3_{cat}h)$ at 235° C. Catalysts of the invention, result in EO-space-time-yields up to 238.3 $kg_{EO}/(m^3_{cat}h)$ at 230° C. and 305.6 $kg_{EO}/(m^3_{cat}h)$ at 235° C. It can further be seen from the numbers at each of the black squares that the EO-space-time-yields tend to increase from the top left part to the bottom right part of FIG. 1.

An EO-space-time yield of at least 200 $kg_{EO}/(m^3_{cat}h)$ was reached at 235° C. with all those catalysts which are below the straight dashed line of FIG. 1.

An EO-space-time yield of more than 185 $kg_{EO}/(m^3_{cat}h)$ was reached at 230° C. with all those catalysts which are below the bold straight dashed line of FIG. 1.

EXAMPLES

Abbreviations

- $AW_{Si}$ atomic weight of Si in g/mol
- $AW_{Ca}$ atomic weight of Ca in g/mol
- $AW_{Mg}$ atomic weight of Mg in g/mol
- $AW_{Cs}$ atomic weight of Cs in g/mol
- $AW_{Re}$ atomic weight of Re in g/mol
- $AW_{W}$ atomic weight of W in g/mol
- $Si_{Al2O3}$ weight of silicon per total support weight in ppm
- $Ca_{Al2O3}$ weight of calcium per total support weight in ppm
- $Mg_{Al2O3}$ weight of magnesium per total support weight in ppm
- $Na_{Al2O3}$ weight of sodium per total support weight in ppm
- $K_{Al2O3}$ weight of potassium per total support weight in ppm
- $Fe_{Al2O3}$ weight of iron per total support weight in ppm
- $Ag_{CAT}$ weight of silver per total catalyst weight in wt-%
- $K_{CAT}$ weight of potassium per total catalyst weight in ppm
- $Li_{CAT}$ weight of lithium per total catalyst weight in ppm
- $S_{CAT}$ weight of sulfur per total catalyst weight in ppm
- $W_{CAT}$ weight of tungsten per total catalyst weight in ppm
- $Cs_{CAT}$ weight of cesium per total catalyst weight in ppm
- $Re_{CAT}$ weight of rhenium per total catalyst weight in ppm
- $K_{ADD}$ weight of potassium per total catalyst weight in ppm added to the catalyst from the applied impregnation solutions
- EC ethyl chloride
- EO ethylene oxide 1. Characterization Methods 1.1 Analysis of Total Amount of Ca-, Mg-, Si-, Fe-, K-, and Na-Contents in Alumina Carriers 1.1.1 Sample Preparation for Measurement of Ca, Mg, Si and Fe Approximately 100-200 mg (at an error margin of ±0.1 mg) of the aluminum oxide carrier sample were weighted into a platinum crucible. 1.0 g of lithium metaborate ($LiBO_2$) was added. The mixture was melted in an automated fusion apparatus with a temperature ramp up to max. 1150° C.

After cooling down, the melt was dissolved in deionized water by careful heating. Then, 10 ml of semi-concentrated hydrochloric acid (concentrated HCl diluted with deionized water, volume ratio 1:1 corresponds to about 6M) was added. Finally, the solution was filled up to a volume of 100 ml with deionized water.

1.1.2 Measurement of Ca, Mg, Si and Fe

Ca, Mg, Si and Fe from the sample solution 1.1.1 were determined by Inductively Coupled Plasma-Optical Emission Spectroscopy (ICP-OES).

Apparatus: ICP-OES Varian Vista Pro

Parameters:

- Wavelengths [nm]: Ca 317.933
  - Mg 285.213
  - Si 251.611
  - Fe 238.204
- Integration time: 10 s
- Nebulizer: Conikal 3 ml
- Nebulizer pressure: 270 kPa
- Pump rate: 30 rpm
- Calibration: external (matrix-matched standards)

1.1.3 Sample Preparation for Measurement of K and Na

Approximately 100-200 mg (at an error margin of ±0.1 mg) of the aluminum oxide carrier sample were weighted into a platinum dish. 10 ml of a mixture of concentrated $H_2SO_4$ and deionized water (volume ratio 1:4), and 10 ml hydrofluoric acid (40%) was added. The platinum dish was placed on a sand bath and boiled down to dryness. After cooling down the platinum dish, the residue was dissolved in deionized water by careful heating. Then 5 mL of semi-concentrated hydrochloric acid (concentrated HCl diluted with deionized water, volume ratio 1:1 corresponds to about 6M) were added. Finally, the solution was filled up to a volume of 50 ml with deionized water.

1.1.4 Measurement of K and Na

Determination of K and Na in the sample solution 1.1.3 was carried out by Flame Atomic Absorption Spectroscopy (F-AAS).

Apparatus: F-AAS Shimadzu AA-7000

Parameters:

- Wavelengths [nm]: K 766.5 Na 589.0
- Gas: Air/acetylene
- Slit width: 0.7 nm (K)/0.2 nm (Na)
- Nebulizer pressure: 270 kPa
- Calibration: external (matrix-matched standards)

2. Alumina Supports

Si-, Ca- Mg-, Na-, K- and Fe-contents in the alumina support [ppm] per total weight of the support, support BET surface area and support water uptake are summarized in Table 1.

TABLE 1

Total Si-, Ca-, Mg-, Na-, K- and Fe- contents in the alumina support [ppm] per total weight of the support, support BET surface area [$m^2/g$], and support water uptake [ml/g].

| | A | B |
|---|---|---|
| $Si_{Al2O3}$ [ppm] | 100 | 500 |
| $Ca_{Al2O3}$ [ppm] | 300 | 400 |
| $Mg_{Al2O3}$ [ppm] | 100 | 200 |
| $Na_{Al2O3}$ [ppm] | 50 | 100 |
| $K_{Al2O3}$ [ppm] | 85 | 185 |
| $Fe_{Al2O3}$ [ppm] | <100 | 100 |
| x [dimensionless][1)] | 0.31 | 0.98 |
| BET surface area [$m^2/g$] | 2.08 | 2.02 |
| Water uptake [ml/g] | 0.46 | 0.52 |

[1)] $x = Si_{Al2O3}/AW_{Si}/(Ca_{Al2O3}/AW_{Ca} + Mg_{Al2O3}/AW_{Mg})$

A skilled person is well familiar with methods for preparing such alumina supports. He would rely on the general knowledge about the preparation of alumina supports in order to provide the desired BET surface area and water uptake. The preparation of alumina supports is, for example, described in EP 3 254 756 A1. BET surface area can be adjusted, for example, by combining two alpha alumina particles of different sizes, when the carrier is prepared (see, e.g. EP 0 902 726 B1 or WO 2011/153390 A2). As pointed out in WO 2012/143559 A1, an increase in the porosity can be achieved using organic additives having a placeholder function, thereby obtaining size distributions which are directly related to the grain sizes of the raw materials used. Additional methods for preparing support materials are described in WO 2012/143559 A1 and WO 2012/143557 A1. It is appreciated that the alumina support may have any of pore size distributions known in the prior art. Examples of suitable support pore size distributions are described in U.S. Pat. Nos. 7,714,152, 7,932,408, 7,977,274, EP 1 511 563 B1, WO 2006/133183, WO 2010/123729.

3. Preparation of Catalysts 3.1 Production of the Silver Complex Solution

Ag-Complex Solution CS-1:

705.35 g DI $H_2O$ were mixed with 789.04 g of ethylene diamine (purity>99%, Merck) under stirring to form an aqueous ethylenediamine solution. The reaction temperature was maintained below 35° C. using cooling. To the resulting aqueous ethylenediamine solution, 43.13 g of 1 wt % aqueous KOH solution were added under stirring. The resulting mixture was cooled to a temperature of 22° C. to form an aqueous KOH ethylenediamine mixture. To the resulting mixture, 512.43 g of oxalic acid dihydrate were added under stirring. The reaction temperature was maintained at a temperature below 40° C. using cooling to produce an aqueous KOH/oxalic acid/ethylenediamine solution. The reaction temperature was cooled down to a temperature of 25° C. To the resulting aqueous KOH/oxalic acid/ethylenediamine solution, 905.75 g of high purity $Ag_2O$ (purity=99.9% by weight) were added under stirring. The reaction temperature was maintained at a temperature below 40° C. using cooling. After addition of the entire amount of $Ag_2O$ the reaction was stirred for further 3 hours while reaction temperature decreased to 32° C. Subsequently, the reaction mixture was centrifuged to remove a minor amount of not dissolved solid. The resulting Ag complex solution had a density of 1.531 g/ml and an Ag-content of 29.6% by weight.

Similarly, further silver complex solution batches CS-2-CS-4 were prepared with amounts of ingredients as listed in Table 2.

TABLE 2

Preparations and properties of Ag complex solutions

| | CS-1 | CS-2 | CS-3 | CS-4 |
|---|---|---|---|---|
| Ethylene Diamine [g] | 789.04 | 789.05 | 663.94 | 604.82 |
| $H_2O$ [g] | 705.35 | 688.14 | 586.29 | 540.65 |
| 1 wt % KOH [g] | 43.13 | 60.33 | 43.50 | 33.04 |
| Oxalic acid dihydrate [g] | 512.43 | 512.44 | 431.19 | 392.78 |
| $Ag_2O$ [g] | 905.75 | 950.75 | 800.01 | 728.26 |
| Ag-content [wt %] | 29.6 | 29.6 | 29.6 | 29.5 |
| Density [g/ml] | 1.531 | 1.529 | 1.529 | 1.530 |
| Target K in Ag complex solution [ppm] | 100 | 140 | 120 | 100 |

3.2 Preparation of Ag-Containing Intermediate Products (1$^{st}$ Impregnation Step)

An amount of support A or B listed in Table 3 was placed into a 2 L glass flask. The flask was attached to a rotary evaporator which was set under vacuum pressure of 30 mbar. The rotary evaporator system was set in rotation of 30 rpm. An amount of silver complex solution CS1-CS4 listed in Table 3 prepared according to step 3.1 was added onto support A or B over 15 minutes under vacuum of 30 mbar. After addition of the silver complex solution, the rotary evaporator system was continued to rotate under vacuum for another 15 minutes. The impregnated support was then left in the apparatus at room temperature and atmospheric pressure for 1 hour and mixed gently every 15 minutes. The impregnated support was calcined for 12 minutes at 290° C. under 23 $m^3$/h flowing nitrogen in a calcination oven to yield Ag-containing intermediate products.

TABLE 3

Support and amounts of ingredients used for the preparation of Ag-containing intermediate products 3.2.1-3.2.6.

| | Intermediate 3.2.1 | Intermediate 3.2.2 | Intermediate 3.2.3 | Intermediate 3.2.4 |
|---|---|---|---|---|
| Alumina support | Support A | Support A | Support A | Support B |
| Amount of support [g] | 261.2 | 262.0 | 261.1 | 350.2 |
| Ag-complex solution | CS-1 | CS-2 | CS-3 | CS-4 |
| Amount of Ag-complex solution [g] | 174.8219 | 174.7361 | 174.1359 | 264.6818 |
| Ag-content in Ag-containing intermediate [wt %] | 16.5 | 16.5 | 16.5 | 18.2 |
| K-content in Ag-containing intermediate added from Ag complex solution [ppm] | 56 | 78 | 67 | 61 |
| K-content in Ag-containing intermediate from the used alumina support [ppm] | 71 | 71 | 71 | 151 |
| Total K-content in Ag-containing intermediate [ppm] | 127 | 149 | 138 | 213 |

3.3. Preparation of Final Catalysts ($2^{nd}$ Impregnation Step)

An amount of Ag-containing intermediate products 3.2.1-3.2.4 listed in Table 4 were placed into a 2 L glass flask. The flask was attached to a rotary evaporator which was set under vacuum pressure of 30 mbar. The rotary evaporator system was set in rotation of 80 rpm. An amount of the silver complex solution CS-1-CS-4 listed in Table 4 prepared according to step 3.1 was mixed with an amount of promoter solution I listed in Table 4, an amount of promoter solution II listed in Table 4, an amount of promoter solution III listed in Table 4. Promoter solution I was made from dissolving lithium nitrate (FMC, 99.3%) and ammonium sulfate (Merck, 99.4%) in DI water to achieve target Li and S contents listed in Table 4. Promoter solution II was made from dissolving tungstic acid (HC Starck, 99.99%) in DI water and cesium hydroxide in water (HC Starck, 50.42%) to achieve target Cs and W contents listed in Table 4. Promoter solution III was made from dissolving ammonium perrhenate (Engelhard, 99.4%) in DI water to achieve target Re content listed in Table 4. The combined impregnation solution containing silver complex solution, promoter solutions I, II, and III was stirred for 5 minutes. The combined impregnation solution was added onto the silver-containing intermediate products 3.2.1.-3.2.4 over 15 minutes under vacuum of 80 mbar. After addition of the combined impregnation solution, the rotary evaporator system was continued to rotate under vacuum for another 15 minutes. The impregnated support was then left in the apparatus at room temperature and atmospheric pressure for 1 hour and mixed gently every 15 minutes. The impregnated material was calcined for 10 minutes at 290° C. under 23 $m^3/h$ flowing nitrogen in a calcination oven to yield the final catalysts.

TABLE 4

Catalyst name and amounts of ingredients used for preparation of catalysts 3.3.1-3.3.3 and 3.3.15.

| Catalyst | 3.3.1 | 3.3.2 | 3.3.3 | 3.3.15 |
|---|---|---|---|---|
| Ag-containing Intermediate from Table 3 | 3.2.1 | 3.2.2 | 3.2.3 | 3.2.4 |
| Amount of Ag-containing Intermediate [g] | 105.7 | 105.5 | 105.6 | 200.8 |
| Ag-complex solution | CS-1 | CS-2 | CS-3 | CS-4 |
| Amount of Ag-complex solution [g] | 41.3908 | 41.3282 | 41.3602 | 90.8649 |
| Amount of promoter solution I [g] | 1.9493 | 1.5425 | 1.9479 | 3.7653 |
| Li-/S-content in promoter solution I [wt %] | 2.85/0.21 | 2.85/0.21 | 2.85/0.21 | 2.85/0.21 |
| Amount of promoter solution II [g] | 1.5760 | 2.1243 | 1.8504 | 4.1106 |
| Cs-/W-content in promoter solution II [wt %] | 6.0/3.0 | 5.56/3.0 | 5.75/3.0 | 6.11/3.0 |
| Amount of promoter solution III [g] | 2.7155 | 2.7113 | 3.0327 | 6.1709 |
| Re-content in promoter solution III [wt %] | 3.7 | 3.7 | 3.7 | 3.7 |
| Ag-content in the catalyst [wt %] | 25.1 | 25.1 | 25.1 | 27.8 |
| $K_{ADD}$ [ppm] K-content in the catalyst added from Ag complex solution used in the $1^{st}$ impregnation step and from the impregnation solution used in the $2^{nd}$ impregnation step | 85 | 119 | 102 | 94 |
| K-content in the catalyst from the used alumina support [ppm] | 63 | 63 | 63 | 133 |
| $K_{CAT}$ [ppm] Total K-content in the catalyst | 148 | 182 | 165 | 227 |

Further catalysts were prepared similarly to catalysts 3.3.1-3.3.3, 3.3.15 with catalyst compositions listed in Table 5. Promoter solutions I and III always used the same Li/S- and Re-contents as listed in Table 4. W-content in promoter solution II was fixed at 3 wt %. Cs-content in promoter solution II was varied to achieve a Cs/W ratio according to Table 5. Amounts of Ag complex solutions and promoter solutions I, II, and III were adjusted to achieve target Ag and promoter contents as listed in Table 5.

TABLE 5

Catalyst compositions (Ag-contents are reported in percent by weight of total catalyst, dopant values are reported in parts per million by weight of total catalyst)

| Example | Support | Ag-complex solution | Ag-intermediate | $Ag_{CAT}$ [wt-%] | $Li_{CAT}$ [ppm] | $S_{CAT}$ [ppm] | $W_{CAT}$ [ppm] | $Cs_{CAT}$ [ppm] | $Re_{CAT}$ [ppm] | $K_{ADD}$ [ppm] | $K_{CAT}$ [ppm] |
|---|---|---|---|---|---|---|---|---|---|---|---|
| 3.3.1 | A | CS-1 | 3.2.1 | 25.1 | 470 | 35 | 400 | 800 | 850 | 85 | 148 |
| 3.3.2 | A | CS-2 | 3.2.2 | 25.1 | 470 | 35 | 540 | 1000 | 850 | 119 | 182 |
| 3.3.3 | A | CS-3 | 3.3.3 | 25.1 | 470 | 35 | 470 | 900 | 950 | 102 | 165 |
| 3.3.4 | A | CS-1 | 3.2.1 | 25.1 | 470 | 35 | 540 | 1000 | 1050 | 85 | 148 |
| 3.3.5 | A | CS-2 | 3.2.2 | 25.1 | 470 | 35 | 540 | 800 | 1050 | 119 | 182 |
| 3.3.6 | A | CS-2 | 3.2.2 | 25.1 | 470 | 35 | 400 | 1000 | 1050 | 119 | 182 |
| 3.3.7 | A | CS-2 | 3.2.2 | 25.1 | 470 | 35 | 400 | 800 | 1050 | 119 | 182 |
| 3.3.8 | A | CS-2 | 3.2.2 | 25.1 | 470 | 35 | 400 | 1000 | 850 | 119 | 182 |
| 3.3.9 | A | CS-2 | 3.2.2 | 25.1 | 470 | 35 | 540 | 800 | 850 | 119 | 182 |
| 3.3.10 | A | CS-1 | 3.2.1 | 25.1 | 470 | 35 | 400 | 1000 | 1050 | 85 | 148 |

TABLE 5-continued

Catalyst compositions (Ag-contents are reported in percent by weight of total catalyst, dopant values are reported in parts per million by weight of total catalyst)

| Example | Support | Ag-complex solution | Ag-intermediate | $Ag_{CAT}$ [wt-%] | $Li_{CAT}$ [ppm] | $S_{CAT}$ [ppm] | $W_{CAT}$ [ppm] | $Cs_{CAT}$ [ppm] | $Re_{CAT}$ [ppm] | $K_{ADD}$ [ppm] | $K_{CAT}$ [ppm] |
|---|---|---|---|---|---|---|---|---|---|---|---|
| 3.3.11 | A | CS-1 | 3.2.1 | 25.1 | 470 | 35 | 540 | 800 | 1050 | 85 | 148 |
| 3.3.12 | A | CS-1 | 3.2.1 | 25.1 | 470 | 35 | 540 | 1000 | 850 | 85 | 148 |
| 3.3.13 | A | CS-3 | 3.2.3 | 25.1 | 470 | 35 | 540 | 800 | 850 | 102 | 165 |
| 3.3.14 | A | CS-1 | 3.2.1 | 25.1 | 470 | 35 | 540 | 900 | 850 | 85 | 148 |
| 3.3.15 | B | CS-4 | 3.2.4 | 27.8 | 470 | 35 | 540 | 1100 | 1000 | 94 | 227 |
| 3.3.16 | B | CS-4 | 3.2.4 | 27.8 | 470 | 35 | 540 | 950 | 850 | 94 | 227 |
| 3.3.17 | B | CS-4 | 3.2.4 | 27.8 | 470 | 35 | 540 | 1250 | 850 | 94 | 227 |
| 3.3.18 | B | CS-4 | 3.2.4 | 27.8 | 470 | 35 | 540 | 950 | 1150 | 94 | 227 |
| 3.3.19 | B | CS-4 | 3.2.4 | 27.8 | 470 | 35 | 540 | 1250 | 1150 | 94 | 227 |
| 3.3.20 | B | CS-4 | 3.2.4 | 27.8 | 470 | 35 | 540 | 950 | 1000 | 94 | 227 |
| 3.3.21 | B | CS-4 | 3.2.4 | 27.8 | 470 | 35 | 540 | 1250 | 1000 | 94 | 227 |
| 3.3.22 | B | CS-4 | 3.2.4 | 27.8 | 470 | 35 | 540 | 1100 | 850 | 94 | 227 |
| 3.3.23 | B | CS-4 | 3.2.4 | 27.8 | 470 | 35 | 540 | 1100 | 1150 | 94 | 227 |

TABLE 6

Key catalyst properties with respect to claims

| Example | Support BET surface area [m²/g] | c(Cs) [mmol/kg] | c(Re) [mmol/kg] | c(W) [mmol/kg] | c(Cs) − c(Re) − c(W) [mmol/kg] | x [1)] [dimensionless] |
|---|---|---|---|---|---|---|
| 3.3.1 | 2.08 | 6.02 | 4.56 | 2.18 | −0.72 | 0.31 |
| 3.3.2 | 2.08 | 7.52 | 4.56 | 2.94 | 0.02 | 0.31 |
| 3.3.3 | 2.08 | 6.77 | 5.10 | 2.56 | −0.89 | 0.31 |
| 3.3.4 | 2.08 | 7.52 | 5.64 | 2.94 | −1.05 | 0.31 |
| 3.3.5 | 2.08 | 6.02 | 5.64 | 2.94 | −2.56 | 0.31 |
| 3.3.6 | 2.08 | 7.52 | 5.64 | 2.18 | −0.29 | 0.31 |
| 3.3.7 | 2.08 | 6.02 | 5.64 | 2.18 | −1.80 | 0.31 |
| 3.3.8 | 2.08 | 7.52 | 4.56 | 2.18 | 0.78 | 0.31 |
| 3.3.9 | 2.08 | 6.02 | 4.56 | 2.94 | −1.48 | 0.31 |
| 3.3.10 | 2.08 | 7.52 | 5.64 | 2.18 | −0.29 | 0.31 |
| 3.3.11 | 2.08 | 6.02 | 5.64 | 2.94 | −2.56 | 0.31 |
| 3.3.12 | 2.08 | 7.52 | 4.56 | 2.94 | 0.02 | 0.31 |
| 3.3.13 | 2.08 | 6.02 | 4.56 | 2.94 | −1.48 | 0.31 |
| 3.3.14 | 2.08 | 6.77 | 4.56 | 2.94 | −0.73 | 0.31 |
| 3.3.15 | 2.02 | 8.28 | 5.37 | 2.94 | −0.03 | 0.98 |
| 3.3.16 | 2.02 | 7.15 | 4.56 | 2.94 | −0.35 | 0.98 |
| 3.3.17 | 2.02 | 9.40 | 4.56 | 2.94 | 1.90 | 0.98 |
| 3.3.18 | 2.02 | 7.15 | 6.18 | 2.94 | −1.97 | 0.98 |
| 3.3.19 | 2.02 | 9.40 | 6.18 | 2.94 | 0.29 | 0.98 |
| 3.3.20 | 2.02 | 7.15 | 5.37 | 2.94 | −1.16 | 0.98 |
| 3.3.21 | 2.02 | 9.40 | 5.37 | 2.94 | 1.10 | 0.98 |
| 3.3.22 | 2.02 | 8.28 | 4.56 | 2.94 | 0.77 | 0.98 |
| 3.3.23 | 2.02 | 8.28 | 6.18 | 2.94 | −0.84 | 0.98 |

[1)] $x = Si_{Al2O3}/AW_{Si}/(Ca_{Al2O3}/AW_{Ca} + Mg_{Al2O3}/AW_{Mg})$

4. Catalyst Testing

The catalyst screening was performed in a 16-fold parallel reactor system. Every reactor was simultaneously supplied with the same inlet gas, at same temperature and same pressure.

The reactor tubes were composed of stainless steel (1.4841) and had a length of 290 mm with an outer diameter of 10 mm and an inner diameter of 4.5 mm. The isothermal zone of the reactor has a length of 70 mm and this was heated using an indirect electrical heating. 1 mL catalyst with a particle size of 250 μm to 315 μm was placed in the isothermal zone of the reactor tube.

The filling scheme of the reactor tube is described in table 7. The filling scheme is a stacked bed with five individual zones. From reactor top to bottom the reactor filling consists of two inert stacks from steatite beads and quartz particles, followed by the catalyst located in the isothermal zone in the center of the reactor tube, followed by another two inert stacks, consisting of quartz particles and steatite beads. Zone 5 represents the top of the reactor tube, where the inlet gas was introduced into the reactor tube. The reactors are operated in once-through mode.

TABLE 7

Reactor tube filling

| Zone | Height [mm] | Material | Particle size [μm] |
|---|---|---|---|
| 1 | 0-70 | steatite beads | 315-500 |
| 2 | 70-90 | quartz particles | 100-350 |
| 3 | 90-153 | catalyst | 250-315 |
| 4 | 153-173 | quartz particles | 100-350 |
| 5 | 173-290 | steatite beads | 315-500 |

The experiments were carried out at a reactor pressure of 15 bar g, at a gas hourly space velocity (GHSV) of about 4530 $h^{-1}$ and at reactor temperatures of 220° C. to 260° C. The inlet gas consisted of 35 vol. % ethylene, 7 vol. % oxygen, 5 vol. % argon and ethylene chloride (EC), which was dosed over a range of 1.3 ppmv to 3.3 ppmv. Nitrogen was used as carrier gas and argon as an internal standard.

The reactor outlet gas was quenched with nitrogen at a ratio of approximately 5:1 and was analyzed via online gas chromatography (GC).

Catalysts were tested at reactor temperatures of 230° C. or 235° C. and at EC concentrations ranging from 1.3 ppmv to 3.3 ppmv to optimize EO-selectivity. The results of the catalyst screening tests are shown in tables 8 and 9. EC concentrations in the tables 8 and 9 correspond to optimized EO-selectivity.

TABLE 8

Test reaction results

| | reactor temperature: 230° C. time on stream: 879.4-950.4 hours | | | | | reactor temperature: 235° C. time on stream: 950.4-1025.4 hours | | | | |
|---|---|---|---|---|---|---|---|---|---|---|
| Ex. | EC [ppm] | S[1] | STY[2] | X[3] | Y[4] | EC [ppm] | S[1] | STY[2] | X[3] | Y[4] |
| 3.3.1 | 1.9 | 87.6 | 189.6 | 6.9 | 6.0 | 2.3 | 87.2 | 249.8 | 9.1 | 7.9 |
| 3.3.2 | 1.3 | 88.2 | 123.6 | 4.4 | 3.9 | 1.3 | 86.9 | 146.0 | 5.3 | 4.6 |
| 3.3.3. | 1.5 | 89.4 | 190.4 | 6.8 | 6.0 | 1.9 | 88.6 | 254.1 | 9.1 | 8.1 |
| 3.3.4 | 1.9 | 89.7 | 200.0 | 7.1 | 6.4 | 2.1 | 89.2 | 249.5 | 8.9 | 7.9 |
| 3.3.5 | 2.7 | 89.4 | 201.0 | 7.2 | 6.5 | 3.1 | 89.1 | 268.7 | 9.7 | 8.6 |
| 3.3.6 | 1.5 | 89.0 | 162.3 | 6.0 | 5.4 | 1.5 | 88.1 | 202.5 | 7.6 | 6.7 |
| 3.3.7 | 2.5 | 88.8 | 205.8 | 7.5 | 6.7 | 2.7 | 88.2 | 263.3 | 9.7 | 8.5 |
| 3.3.8 | 1.3 | 86.3 | 118.2 | 4.4 | 3.8 | 1.3 | 84.9 | 140.9 | 5.4 | 4.6 |
| 3.3.9 | 1.9 | 89.1 | 198.2 | 7.2 | 6.4 | 1.5 | 88.8 | 209.3 | 7.6 | 6.8 |
| 3.3.10 | 1.5 | 88.9 | 190.7 | 7.0 | 6.2 | 1.5 | 88.0 | 229.3 | 8.4 | 7.4 |
| 3.3.11 | 2.7 | 88.7 | 225.1 | 8.2 | 7.3 | 2.7 | 88.3 | 276.9 | 10.1 | 9.0 |
| 3.3.12 | 1.5 | 88.8 | 185.4 | 6.7 | 5.9 | 1.5 | 88.6 | 227.1 | 8.2 | 7.3 |
| 3.3.13 | 1.5 | 89.3 | 188.1 | 6.6 | 5.9 | 1.9 | 88.7 | 249.2 | 8.8 | 7.8 |
| 3.3.14 | 1.5 | 89.1 | 190.0 | 6.8 | 6.1 | 1.5 | 88.4 | 226.7 | 8.2 | 7.3 |

[1]EO-selectivity [%]
[2]EO-space-time-yield [$kg_{EO}/(m^3_{cat}h)$]
[3]EO-conversion [%]
[4]EO-yield [%]

TABLE 9

Test reaction results

| | reactor temperature: 230° C. time on stream: 311.3-379.5 hours | | | | | reactor temperature: 235° C. time on stream: 379.5-448.6 hours | | | | |
|---|---|---|---|---|---|---|---|---|---|---|
| Ex. | EC [ppm] | S[1] | STY[2] | X[3] | Y[4] | EC [ppm] | S[1] | STY[2] | X[3] | Y[4] |
| 3.3.15 | 1.9 | 87.6 | 214.6 | 7.9 | 6.9 | 1.9 | 87.1 | 256.0 | 9.5 | 8.2 |
| 3.3.16 | 1.9 | 87.6 | 217.3 | 8.0 | 7.0 | 1.9 | 87.2 | 258.4 | 9.6 | 8.4 |
| 3.3.17 | 1.3 | 85.7 | 152.1 | 5.7 | 4.9 | 1.7 | 85.2 | 237.6 | 9.0 | 7.7 |
| 3.3.18 | 2.5 | 88.1 | 238.3 | 8.8 | 7.8 | 2.9 | 87.3 | 305.6 | 11.5 | 10.0 |
| 3.3.19 | 1.9 | 86.7 | 226.1 | 8.4 | 7.3 | 1.9 | 86.1 | 269.8 | 10.1 | 8.7 |
| 3.3.20 | 1.9 | 87.9 | 208.9 | 7.6 | 6.7 | 2.7 | 87.6 | 297.8 | 10.9 | 9.6 |
| 3.3.21 | 1.3 | 86.1 | 132.1 | 4.9 | 4.2 | 1.7 | 85.5 | 241.1 | 9.0 | 7.7 |
| 3.3.22 | 1.9 | 86.1 | 232.8 | 8.4 | 7.2 | 1.9 | 86.0 | 278.3 | 10.1 | 8.7 |
| 3.3.23 | 1.9 | 88.0 | 222.8 | 8.1 | 7.1 | 1.9 | 87.7 | 261.7 | 9.6 | 8.4 |

[1]EO-selectivity [%]
[2]EO-space-time-yield [$kg_{EO}/(m^3_{cat}h)$]
[3]EO-conversion [%]
[4]EO-yield [%]

The invention claimed is:

1. A catalyst effective in the oxidative conversion of ethylene to ethylene oxide, comprising an alumina support and 23 to 30% of silver based on the weight of the catalyst, the catalyst meeting the following limitations (i) to (v):

(i) an amount of cesium c(Cs) in mmol per Kg of catalyst of 5.5 to 8.5;

(ii) an amount of rhenium c(Re) in mmol per Kg of catalyst of 4.0 to 7.0;

(iii) an amount of tungsten c(W) in mmol per Kg of catalyst of 1.6 to 3.25;

(iv) a silicon to alkaline earth metal molar ratio x of not higher than 1.80;

(v) $c(Cs)-c(Re)-c(W)\leq 4\cdot x-0.5$;

wherein x is 0.1 to 1.46.

2. The catalyst according to claim 1, wherein $$c(Cs)-c(Re)-c(W)\leq 4\cdot x-1.3.$$

3. The catalyst according to claim 2, wherein $$c(Cs)-c(Re)-c(W)\leq 2.35\cdot x-1.3.$$

4. The catalyst according to claim 1, comprising an amount of potassium c(K) in mmol per Kg of catalyst of 2.6 to 10.3.

5. The catalyst according to claim 1, comprising an amount of sodium c(Na) in mmol per Kg of catalyst of 0.2 to 10.8.

6. The catalyst according to claim 1, comprising an amount of lithium c(Li) in mmol per Kg of catalyst of 43 to 86.

7. The catalyst according to claim 1, comprising an amount of sulfur c(S) in mmol per Kg of catalyst of 0.3 to 3.

8. The catalyst according to claim 1, wherein the Cs:Re:W molar ratio is 12 to 19:9 to 12.5:4 to 6.

9. The catalyst according to claim 1, wherein the alumina support has a water absorption of 0.35 ml/g to 0.70 ml/g.

10. The catalyst according to claim 1, wherein the ratio of water absorption of the alumina support to BET surface area of the alumina support is in the range from 0.18 to 0.33 ml/$m^2$.

* * * * *